US007399635B2

(12) United States Patent
Hellin et al.

(10) Patent No.: US 7,399,635 B2
(45) Date of Patent: Jul. 15, 2008

(54) IMPURITY MEASURING METHOD FOR GE SUBSTRATES

(75) Inventors: David Hellin, Beersel (BE); Ivo Teerlinck, Linden (BE); Jan Van Steenbergen, Kapellen (BE)

(73) Assignees: Interuniversitair Microelektronica Centrum (IMEC), Leuven (BE); UMICORE N.V., Brussels (BE)

( * ) Notice: Subject to any disclaimer, the term of this patent is extended or adjusted under 35 U.S.C. 154(b) by 594 days.

(21) Appl. No.: 11/009,096

(22) Filed: Dec. 10, 2004

(65) Prior Publication Data
US 2005/0170524 A1 Aug. 4, 2005

Related U.S. Application Data

(60) Provisional application No. 60/530,214, filed on Dec. 12, 2003.

(51) Int. Cl.
*G01N 1/00* (2006.01)
(52) U.S. Cl. .............................. 436/5; 436/178; 438/14
(58) Field of Classification Search .............. 428/312.6; 436/178; 156/8; 438/200
See application file for complete search history.

(56) References Cited

U.S. PATENT DOCUMENTS

| 3,979,240 | A | * | 9/1976 | Ghezzo | ....................... 216/101 |
| 4,990,459 | A | | 2/1991 | Maeda et al. | |
| 6,620,632 | B2 | * | 9/2003 | Koveshnikov et al. | .......... 438/14 |
| 2002/0052072 | A1 | * | 5/2002 | Hirose | ........................ 438/200 |
| 2004/0076813 | A1 | * | 4/2004 | Han et al. | ................ 428/312.6 |

FOREIGN PATENT DOCUMENTS

EP 0 339 463 A 2/1989

OTHER PUBLICATIONS

Hellin et al. *Validation of Vapor Phase Decomposition-Droplet Collection-Total Reflection X-ray Fluorescence Spectrometry for Metallic Contamination Analysis of Silicon Wafers*, TXRF 2003 Conference Hyogo, Japan.
Neumann et al. Spectrochimica Acta Part B, vol. 46, *Ultra Trace Analysis of Metallic Contaminations on Silicon Wafer Surfaces by Vapour Phase Decomposition/Total Reflection X-ray Fluorescence*. p. 1369-1377, 1991.
Hellin et al. *Determination of Metallic Contaminants on GE Wafers using direct-and Droplet Sandwich etch-Total Reflection X-ray Fluorescence Spectrometry*, pp. 2093-2104, 2003. Spectrochimica Acta Part B. vol. 58 No. 12; XP002323124.

(Continued)

*Primary Examiner*—Walter D. Griffin
*Assistant Examiner*—Christine T Mui
(74) *Attorney, Agent, or Firm*—Knobbe Martens Olson & Bear LLP

(57) ABSTRACT

The present invention provides an impurity measuring method comprising the steps of dropping a drop of a first solution on the surface of a substrate to be measured, moving the drop dropped on the surface of the substrate so that the drop is kept in contact with the surface and collects an impurity absorbed on the surface, recovering the drop after the movement and analyzing the recovered drop by chemical analysis to determine the type and concentration of the impurity, characterized in that the first solution is phobic to the substrate and the substrate consists substantially of Ge. The method is of particular importance for measuring metallic contamination on the surface of Ge substrates.

29 Claims, 3 Drawing Sheets

OTHER PUBLICATIONS

S. Pahlke et al. *Determination of Ultra Trace Contaminants on Silicon Wafer Surfaces Using Total-Reflection X-ray Flurorescence TXRF "state-of-the-art"*; Spectrochimica Acta Part B, vol. 56 No. 11, Nov. 30, 2001; XP002323125.

A. Shimazaki, et al. *Chemical Analysis of Ultratrace Impurities in SiO2 Films*, Japanese Journal of Applied Physics, Publication Office Japanese Journal of Applied Physics, Tokyo, Japan, Sep. 30, 2004, pp. 281-284; XP002138722.

McDaniel, et al. *Impurity Measurements in Semiconductor Materials Using Trace Element Accelerator Mass Spectrometry*, Nuclear Instruments & Methods in Physics Research, Section B, Beam Interactions with Materials and Atoms, North Holland Publishing Company, Amsterdam, NL. vol. 190, No. 1-4, May 2002, pp. 826-830; XP004351657.

European Patent Office Search Report, filed in Application No. 04447274, mailed on Apr. 15, 2005.

* cited by examiner

IMPURITY MEASURING METHOD FOR GE SUBSTRATES

RELATED APPLICATION

This application claims the benefit of U.S. Provisional Application No. 60/530,214, filed Dec. 12, 2003, the contents of which are hereby incorporated by reference in their entirety and are hereby made a part of this specification.

FIELD OF THE INVENTION

The present invention relates to a method for impurity measurements on Ge substrates.

BACKGROUND OF THE INVENTION

In microelectronics industry Ge wafers are important substrates with technological applications in optical devices and are very recently introduced as a replacement for Si substrates for advanced Integrated Circuit (IC) devices. In order to realize high performance devices the Ge wafer surface has to be of high purity.

Earlier studies have demonstrated the detrimental effects of metallic contaminants on the electro-physical properties of the Ge surface. Therefore, it is needed to control carefully the metallic contamination during processing of Ge wafers. Specifications for metallic contamination are set to levels below 5E9 at/cm$^2$.

Cleaning recipes have to be developed and performances evaluated by an appropriate analysis methodology. Whereas several studies focused on the optimization of cleaning recipes, there is still a lack in the metallic contamination analysis for Ge wafers.

Direct-Total Reflection X-Ray Fluorescence (D-TXRF) is unrivalled for the direct contamination analysis on Si wafers. The Detection Limits (DL) for this technique have been evaluated also for Ge wafers and are in the order of E10-E11 at/cm$^2$. To meet the more stringent requirements of the IC processing environment further development of the metrology is hence needed.

For the analysis of metallic contamination on Si wafers, the combination of the pre-concentration method of Vapor Phase Decomposition-Droplet Collection (VPD-DC) with micro-volume analytical techniques is a well-established method, which is patented by Maeda et al. (U.S. Pat. No. 4,990,459). The method consists of different subsequent steps. During the VPD step, the native oxide of the Si wafer is etched by an HF fume resulting in a hydrophobic Si surface. In the subsequent DC step the wafer surface is scanned with a micro-droplet of an aqueous mixture to collect the metallic impurities. This droplet can then be analyzed with any wet chemical micro trace analytical technique such as Graphite Furnace-Atomic Absorption Spectrometry (GF-AAS) or Inductive Coupled Plasma-Mass Spectrometry (ICP-MS). Alternatively, the micro-droplet is dried on a carrier substrate and the resulted residue is analyzed by TXRF. The combination of VPD-DC and TXRF for Si wafers is studied in detail by C. Neumann and P. Eichinger (Spectrochim. Acta 46B, p1369, 1991) and presented by D. Hellin et al. ('Validation of VPD-DC for metallic contamination analysis of Si wafers', TXRF2003 Conference, Hyogo, Japan). This technique, however, does not work in case of Ge wafers, because an aqueous mixture is not phobic to Ge and droplet loss occurs during scanning.

For metallic contaminants on small size Ge wafers (100 mm), a pre-concentration method is based on the Droplet Sandwich Etch method (DSE), described by D. Hellin, et al. ('Determination of metallic contaminants on Ge wafers using Direct- and DSE-TXRF spectrometry', In press, Spectrochim. Acta part B (2003)). In this method, a droplet of a chemical mixture is deposited on a clean carrier substrate. The substrate of interest is then placed on the carrier substrate with the side to be analyzed towards the carrier, sandwiching the droplet. Upon removal of the top substrate a part of the chemical mixture remains on the carrier substrate. This liquid can then be analyzed by any micro-volume analytical technique. However, this methodology suffers from severe limitations with respect to automation and scalability to large wafer sizes.

The VPD-DC methodology as described by Maeda et al. requires the surface of the object to be measured to be hydrophobic to allow scanning by an aqueous solution. If the surface of the object is hydrophilic it has to be rendered hydrophobic by a vapor phase treatment.

Since Ge substrates are not hydrophobic, both HCl and HF vapor treatments are tested to render the Ge surface hydrophobic.

This treatment resulted in rather hydrophilic surfaces. The contact angle after the treatments measured by dispensing a micro-droplet of water (in essence) onto the treated surface resulted in values of about 15 deg. Consequently, the Ge surface could not be scanned by the water droplet as it wetted the surface and split into multiple smaller droplets when scanning. In addition, the treated surface cannot be scanned with one of the solutions Maeda proposed: HF, HF+HNO$_3$, HF+H$_2$O$_2$ and HCl+H$_2$O$_2$.

Solutions of HF up to 49 wt. % were tested.

After application of the VPD step, the Ge surface was not phobic to any of these solutions and droplet loss occurred during scanning.

SUMMARY OF THE INVENTION

The present invention provides a method for measuring an impurity upon the surface of a substrate comprising (or consisting of) the steps of:

dropping a drop of a first solution on said surface to be measured, moving the drop dropped on said surface so that the drop is kept in contact with said surface and collects an impurity absorbed on said surface, recovering the drop after the movement, and analyzing the recovered drop by chemical analysis to determine the type and concentration of the impurity, characterized in that the substrate consists essentially of Ge, and in that the first solution is phobic to Ge substrate.

The method is of particular importance for measuring metallic contamination on the surface of Ge substrates.

In a preferred method of the invention, said first solution, also referred to as the "Ge-phobic solution", comprises HCl and/or HBr.

Preferably, said Ge-phobic solution comprises HCl and/or HBr in a concentration of at least about 30 wt. %, or at least about 35 wt. %.

A preferred Ge-phobic solution comprises at least about 37 wt. % HCl.

A preferred Ge-phobic solution comprises at least about 47 wt. % HBr.

Said Ge-phobic solution may further comprise less then about 0.25 wt. % H$_2$O$_2$, or may be free of germanium oxidizing compounds.

A method according to the invention may further comprise an additional step of making the surface of a Ge substrate phobic to the Ge-phobic solution, thereby using a vapor of a second solution.

The second solution, also referred to as VPD-solution, may comprise a halogen.

Said VPD-solution preferably comprises HF, HCl, or HBr or any combination of two or three thereof.

DETAILED DESCRIPTION

Figure 1:
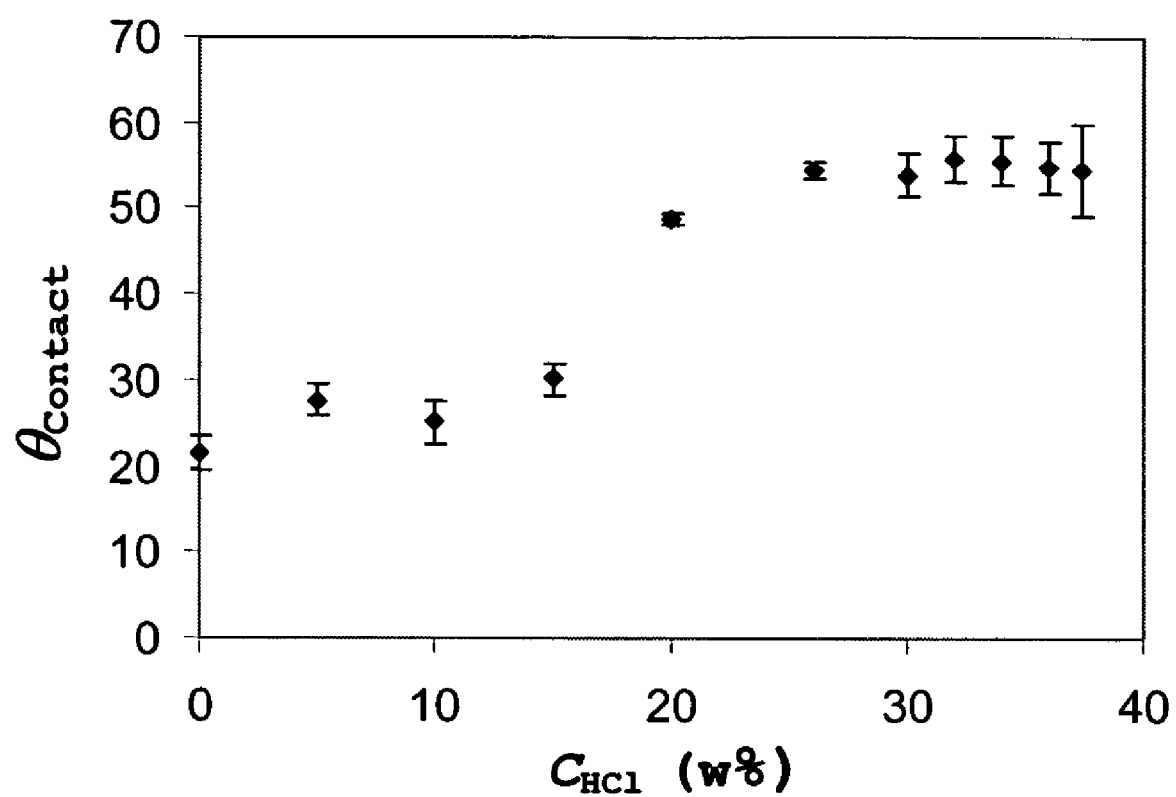
FIG. 1: Contact angle as a function of the HCl concentration in the micro-droplet after HF VPD treatment of the Ge surface.

In a first aspect of the invention, an impurity measuring method for Ge wafers is disclosed, comprising the steps of:
dropping a drop of a solution on the surface of a Ge substrate to be measured, in which said solution is phobic to said Ge substrate;
moving said drop dropped on the surface of said Ge substrate so that said drop is kept in contact with the surface of said Ge substrate and collects an impurity on the surface of said Ge substrate;
recovering said drop after the movement; and
analyzing said recovered drop by chemical analysis to determine the type and concentration of an impurity on the surface of said Ge substrate.

Said method is of particular importance for measuring metallic contamination on the surface of Ge substrates.

In a first embodiment, said Ge-phobic solution comprises HCl or HBr or any combination thereof.

In another embodiment said solution comprises at least 30 wt. % HCl or at least 30 wt. % HBr or any combination thereof.

In another embodiment the solution comprises HCl or HBr or any combination thereof and less then 0.25 wt. % $H_2O_2$.

In a preferred embodiment, said Ge-phobic solution comprises 37 wt. % HCl.

In a second aspect of this invention, an impurity measuring method for Ge wafers is disclosed, said method comprising the steps as disclosed in the first aspect of this invention and an additional step making the surface of a Ge substrate phobic to said impurity collecting solution, using a vapor of a second solution.

In a first embodiment of this second aspect, said Ge-phobic solution comprises HCl or HBr or any combination thereof.

In another embodiment of the second aspect, said solution comprises at least 30 wt. % HCl or at least 30 wt. % HBr or any combination thereof.

In another embodiment of the second aspect, the solution comprises HCl or HBr or any combination thereof and less then 0.25 wt. % $H_2O_2$.

In a preferred embodiment of this second aspect, said Ge-phobic solution comprises 37 wt. % HCl.

In another preferred embodiment of this second aspect, said second solution is of the form HX, in which X is F, Cl, or Br.

Thus, the present invention provides a method for measuring an impurity upon the surface of a substrate, comprising (or consisting of) the steps of:
dropping a drop of a first solution on said surface to be measured,
moving the drop dropped on said surface so that the drop is kept in contact with said surface and collects an impurity absorbed on said surface,
recovering the drop after the movement, and
analyzing the recovered drop by chemical analysis to determine the type and concentration of the impurity, characterized in that said substrate consists substantially of Ge and in that said first solution is phobic to Ge substrates.

In the context of the present invention, the term "substrate essentially of Ge" refers to a Ge substrate, which may have on its surface native germanium oxides, and except in contexts where the native germanium oxides are completely removed, the term "Ge substrate" may also refer to a substrate essentially of Ge.

In the context of the present invention, the term "phobic solution" refers to a solution that does not wet the Ge surface (or which is not absorbed by the Ge substrate). Consequently, the droplet of said solution can be used to scan the Ge surface.

Preferably, in a method of the invention, said first solution, also referred to as Ge-phobic solution, comprises HCl and/or HBr.

Preferably, said Ge-phobic solution comprises:
HCl in a concentration of at least about 20 wt. %, preferably of at least about 25 wt. %, more preferably of at least about 30 wt. %, or at least about 35 wt. %,
HBr in a concentration of at least about 20 wt. %, preferably of at least about 25 wt. %, more preferably of at least about 30 wt. %, or at least about 35 wt. %, or
HCl and HBr in (or to reach) a concentration of at least about 20 wt. %, preferably of at least about 25 wt. %, more preferably of at least about 30 wt. %, or at least about 35 wt. %.

The contact angle can be increased significantly up to 55 degrees by addition of HCl or HBr or any combination thereof to an aqueous phase.

FIG. 1 shows the contact angle values versus the concentration of HCl in the micro-droplet after a HF VPD treatment. From about 20 wt. %, from about 25 wt. %, or from about 30 wt % HCl, the contact angle reaches values of at least 50 degrees.

This is also the case for HBr (not shown in FIG. 1).

A preferred Ge-phobic solution comprises at least about 37 wt. % HCl or at least about 47 wt. % HBr.

A Ge-phobic solution of the invention may further comprise less then about 0.25 wt. % $H_2O_2$, or may be free of germanium oxidizing compounds.

Ge oxidizing compounds in combination with the aqueous phase cause severe Ge etching. These Ge oxidizing compounds may be $H_2O_2$, $HNO_3$, $O_2$, O3, or any compound forming germanium oxides.

In particular, the present invention provides a method for measuring an impurity upon the surface of a Ge substrate comprising (or consisting of) the steps of:
dropping a drop of a solution comprising HCl and/or HBr in a concentration of at least 20 wt. %, preferably of at least 25 wt. %, more preferably of at least 30 wt. %, in particular of (about) 37 wt. %, on said surface,
moving the drop dropped on said surface so that the drop is kept in contact with said surface and collects an impurity absorbed on said surface, recovering the drop after the movement, and analyzing the recovered drop by chemical analysis to determine the type and concentration of the impurity.

In a method of the invention, the movement of the drop may occur at a speed of lower than about 20 mm/s, lower than about 10 mm/s, or about 5 mm/s.

The analysis of the recovered drop may be performed by any wet chemical micro trace analytical technique such as Graphite Furnace-Atomic Absorption Spectrometry (GF-AAS) or Inductive Coupled Plasma-Mass Spectrometry (ICP-MS). Alternatively, the micro-droplet is dried on a carrier substrate and the resulted residue is analyzed by TXRF.

A method according to the invention may comprise, before the dropping step, an additional step of treating the surface of a Ge substrate with a second solution in form of vapour, for etching, at least partially, the native germanium oxides.

Said second solution, also referred to as VPD-solution, preferably comprise a halogen. In particular, said second solution may comprise HF, HCl or HBr or any combination thereof.

By etching, at least partially, the native germanium oxides, the surface of a Ge substrate is rendered more phobic to the phobic solution.

Figure 3A:
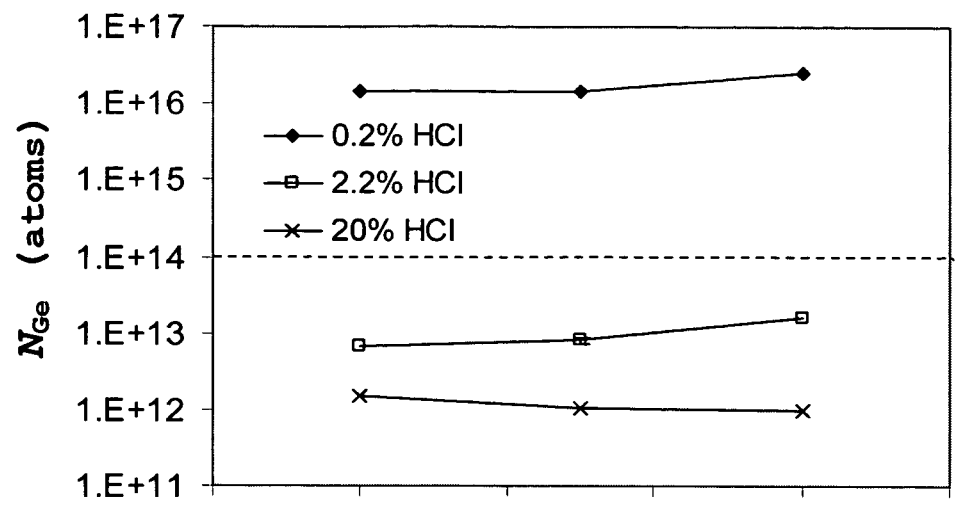
FIG. 3(a): Influence of the HCl concentration and wafer temperature on the removal of the Ge matrix and (b) related TXRF detection efficiency of traces (K, Ca, Sc, Cr, Fe, Ni, Zn all at 2.5E12 atoms)
Figure 3B:
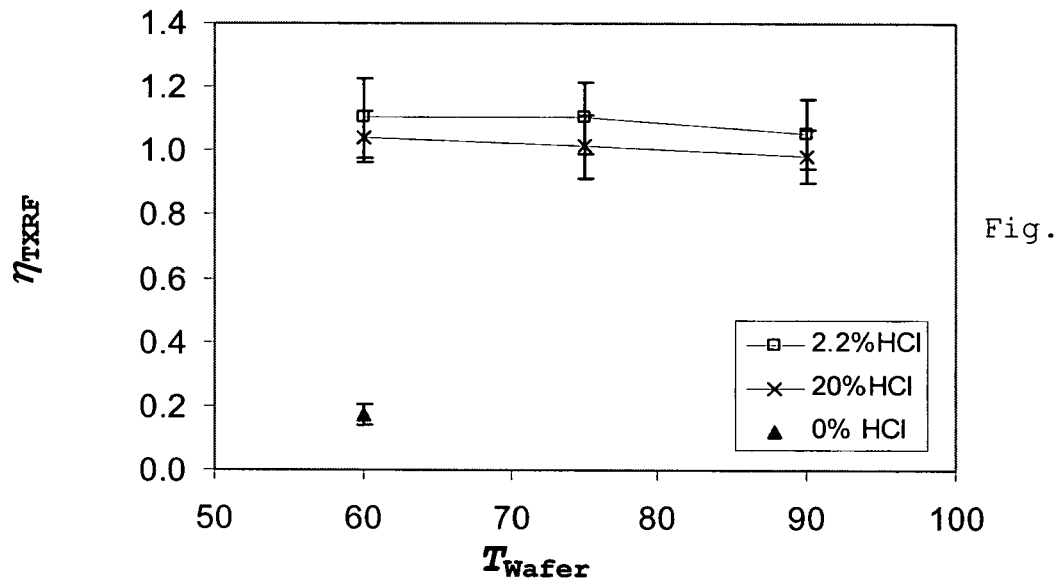

Removal of the Ge matrix increases the TXRF accuracy from a 20% level to 100% values (FIG. 3).

When evaluating the collection efficiency of the method according to the present invention on metal spin coated Ge wafers (K, Ca, Cr, Fe, Ni and Zn, 5E11-1E12 at/cm² each), no metals above the detection limits of TXRF can be measured. Thus, the values for collection efficiency ηColl are determined from the starting concentration CSpin and the detection limits of TXRF measurement tool CDL:

$$\eta_{Coll} \geq \frac{C_{Spin} - C_{DL}}{C_{Spin}}$$

Figure 2:
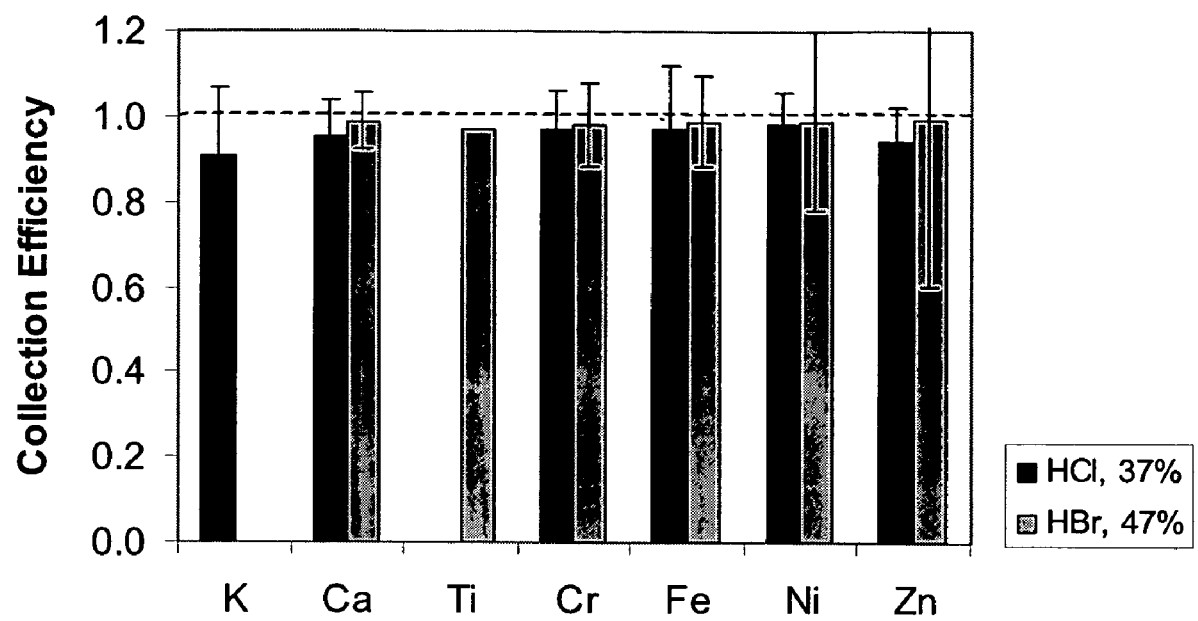
FIG. 2: Collection efficiency of VPD-DC applied on multi-element spin coated Ge wafers using a 37% HCl or 47% HBr DC solution.

FIG. 2 shows collection efficiency values are very close to unity for all of the investigated elements.

Before chemical analysis of the recovered drop, the Ge matrix may be removed at least partially. This may occur by chemical reaction with HCl and/or HBr.

The VPD-DC step results in a micro-droplet containing a large Ge matrix concentration of typically $10^{16}$-$10^{17}$ atoms (i.e. 100-1000 mg/L). This high matrix concentration is incompatible with the analysis of ultra-traces of contaminants within this matrix. Therefore the Ge matrix is removed at least partially, prior to the analysis.

In the case of VPD-DC-TXRF on Si wafers, the Si matrix is removed by a selective volatilization of $SiF_4$ during the dry step.

Ge can however not be removed from aqueous solutions under speciation of $GeF_4$ but must be removed as the volatile $GeCl_4$ or $GeBr_4$. These compounds can be formed in a reaction with HCl and/or HBr. Consequently, during droplet collection using HCl and/or HBr solutions, the Ge matrix reacts already with HCl and/or HBr, resulting in the volatile product, which then is removed by heating the micro-droplet.

FIG. 3 indicates that drying of a Ge containing micro-droplet on a hotplate yields a high Ge matrix removal for HCl concentrations of 2 wt. % or higher. Starting with a Ge amount of $4 \times 10^{16}$ atoms in the 50 μL droplet, the residual Ge concentration in the residue is decreased with more than three orders of magnitude. The method can be applied in a large temperature window temperature of 60-90° C. Removal of the Ge matrix increases the TXRF accuracy from a 20% level to 100% values.

A method according to the invention allows the evaluation of the cleanliness of Ge wafers in a practical and very sensitive manner and should facilitate the development of cleaning recipes.

The invention is described in further details in the following example, which is intended for illustration purposes only, and should not be construed as limiting the scope of the invention in any way.

EXAMPLE

In this example, a 100 mm Ge wafers (Umicore) and 200 mm Si wafers, both with a <100> crystal orientation, were used.

Ge droplet residues standards were prepared by the micro-droplet deposition method.

Standard multi-element solutions with a constant concentration of traces (K, Sc, Cr, Fe, Ni, Zn, all at $2.5 \times 10^{12}$ atoms/50 μL) and a variable Ge concentration were prepared by dilution of ICP-MS calibration standards (1000 μg/mL, nitrate salts, Merck).

Droplets of 50 μL volume were pipetted on hydrophobic Si wafers (contact angle 65 deg) and dried at 50° C. and 100 mbar in a Wafer Surface Preparation System (GeMeTec).

The accuracy of a TXRF measurement was evaluated as the ratio of the measured amount of traces over the theoretical amount expected from the dilution of the standard solution.

The spin coating technique was used to prepare standard wafers.

Multi-element solutions were prepared by dilution of ICP-MS calibration standards (1000 mg/L, nitrate salts, Merck), acidified with HCl (2 vol. % of 37% HCl, Ultrex, Baker).

Portions of 10 mL were pipetted onto the Ge wafers positioned on a high-speed wafer spinner (Laurell WS-400). After 30 seconds, the spinner was run at 3000 rpm for 1 min in order to dry the wafer surface. With this procedure wafers with a target concentration in the order of $1 \times 10^{11}$-$1 \times 10^{12}$ at/cm² were prepared.

In the Ge matrix removal experiments, a Ge standard solution has been prepared in ultra pure water. A Ge wafer piece was etched in a diluted $H_2O_2$ solution (¼$H_2O_2$ (30%, Ashland)/$H_2O$) and the etched Ge amount was determined from differential weighing. Trace amounts of K, Ca, Sc, Cr, Fe, Ni and Zn) were added from a dilution of ICP-MS standard solutions (1000 mg/L, nitrate salts, Merck).

TXRF analysis was performed using a FEI (formerly ATOMIKA) 8300 W system equipped with a W or Mo tube operated at 50 kV and 55 mA.

All measurements were done in WLβ or MoKα excitation mode at 70% of the critical angle, for 1000 s live time. Calibration was applied using a 1 ng Ni micro-droplet type silicon wafer standard (FEI-ATOMIKA).

The VPD-DC preparation was done using an automated Wafer Surface Preparation System (GeMeTec).

The DC step was performed using a 50 μL droplet of HCl (37%, Ashland, Megabit) which scanned the wafer surface twice.

Contact angles were determined by the sessile droplet method using a 5 μL droplet of the tested solution. The contact angle was evaluated from the CCD camera picture using the Laplace-Young equation (Dataphysics, Contact Angle System OCA).

All references cited herein are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The invention claimed is:

1. A method for measuring an impurity upon a surface of a substrate, the method comprising the steps of:
   dropping a drop of a first solution on the surface to be measured;
   moving the drop dropped on the surface so that the drop is kept in contact with the surface and collects an impurity absorbed on the surface;
   recovering the drop after the movement; and
   analyzing the recovered drop by a chemical analysis to determine a type and a concentration of the impurity, wherein the substrate consists essentially of germanium, and wherein the first solution is phobic to the substrate.

2. A method for measuring an impurity upon a surface of a substrate, the method comprising the steps of:
   dropping a drop of a first solution on the surface to be measured, wherein a contact angle of the drop is least 50 degrees,
   moving the drop dropped on the surface so that the drop is kept in contact with the surface and collects an impurity absorbed on the surface,
   recovering the drop after the movement, and
   analyzing the recovered drop by a chemical analysis to determine a type and a concentration of the impurity, wherein the substrate consists essentially of germanium, and wherein the first solution is selected from the group consisting of HCl, HBr, and a combination thereof.

3. The method according to claim 2, wherein a concentration of the HBr, HCl, or combination thereof in the first solution is at least about 30 wt. %.

4. The method according to claim 2, wherein a concentration of the HBr, HCl, or combination thereof in the first solution is at least about 35 wt. %.

5. The method according to claim 2, wherein the first solution comprises about 37 wt. % HCl.

6. The method according to claim 2, wherein the first solution comprises about 47 wt. % HBr.

7. The method according to claim 2, wherein a concentration of the HBr, HCl, or combination thereof in the first solution is at least about 30 wt. %, and wherein a concentration of $H_2O_2$ in the first solution is less than about 0.25 wt. %.

8. The method according to claim 2, wherein a concentration of the HBr, HCl, or combination thereof in the first solution is at least about 30 wt. %, and wherein the first solution is free of germanium oxidizing compounds.

9. The method according to claim 2, wherein a germanium matrix is at least partially removed by a chemical reaction with HCl, HBr, or mixtures thereof, before the step of analyzing is conducted.

10. The method according to claim 2, wherein a germanium matrix is removed by a chemical reaction with HCl, HBr, or combinations thereof.

11. A method for measuring an impurity upon a surface of a substrate, the method comprising the steps of:
    making the surface of the substrate phobic to a first solution by using a vapour of a second solution;
    dropping a drop of the first solution on the surface to be measured;
    moving the drop dropped on the surface so that the drop is kept in contact with the surface and collects an impurity absorbed on the surface;
    recovering the drop after the movement; and
    analyzing the recovered drop by a chemical analysis to determine a type a concentration of the impurity, wherein the substrate consists essentially of germanium, and wherein the first solution is phobic to the substrate.

12. A method for measuring an impurity upon a surface of a substrate, the method comprising the steps of:
    making the surface of the substrate phobic to a first solution by using a vapour of a second solution;
    dropping a drop of the first solution on the surface to be measured;
    moving the drop dropped on the surface so that the drop is kept in contact with the surface and collects an impurity absorbed on the surface;
    recovering the drop after the movement; and
    analyzing the recovered drop by a chemical analysis to determine a type and a concentration of the impurity, wherein the substrate consists essentially of germanium, and wherein the first solution comprises HCl, HBr, or combinations thereof.

13. The method according to claim 12, wherein a concentration of the HBr, HCl, or combination thereof in the first solution is at least about 30 wt. %.

14. The method according to claim 12, wherein a concentration of the HBr, HCl, or combination thereof in the first solution is at least about 35 wt. %.

15. The method according to claim 12, wherein the first solution comprises about 37 wt. % HCl.

16. The method according to claim 12, wherein the first solution comprises about 47 wt. % HBr.

17. The method according to claim 12, wherein a concentration of the HBr, HCl, or combination thereof in the first solution is at least about 30 wt. %, and wherein a concentration of $H_2O_2$ in the first solution is less than about 0.25 wt. %.

18. The method according to claim 12, wherein a concentration of the HBr, HCl, or combination thereof in the first solution is at least about 30 wt. %, and wherein the first solution is free of germanium oxidizing compounds.

19. The method according to claim 12, wherein the second solution comprises a component selected from the group consisting of HF, HCl, HBr, and combinations thereof.

20. The method according to claim 12, wherein a germanium matrix is at least partially removed by a chemical reaction with HCl, HBr, or mixtures thereof, before the step of analyzing is conducted.

21. The method according to claim 12, wherein a germanium matrix is removed by a chemical reaction with HCl, HBr, or combinations thereof.

22. The method according to claim 2, wherein the first solution is phobic to the substrate.

23. The method according to claim 1, wherein a concentration of HBr in the first solution is at least about 30 wt. %.

24. The method according to claim 1, wherein a concentration of HCl in the first solution is at least about 30 wt. %.

25. The method according to claim 1, wherein a concentration of the HBr, HCl, or combination thereof in the first solution is at least about 30 wt. %.

26. The method according to claim 1, wherein a concentration of $H_2O_2$ in the first solution is less than about 0.25 wt. %.

27. The method according to claim 1, wherein the first solution is free of germanium oxidizing compounds.

28. The method according to claim 11, wherein a contact angle of the drop is at least 50 degrees.

29. The method according to claim 12, wherein a contact angle of the drop is at least 50 degrees.

* * * * *

UNITED STATES PATENT AND TRADEMARK OFFICE
CERTIFICATE OF CORRECTION

PATENT NO. : 7,399,635 B2  
APPLICATION NO. : 11/009096  
DATED : July 15, 2008  
INVENTOR(S) : Hellin et al.

Page 1 of 1

It is certified that error appears in the above-identified patent and that said Letters Patent is hereby corrected as shown below:

1. Description of Error

| Column | Line | |
|---|---|---|
| 4 | 55 | Delete "03," and insert -- $O_3$, --, therefor. |
| 7 | 47 (Approx.) | In Claim 2, delete "is" and insert -- is at --, therefor. |

Signed and Sealed this  
Eighth Day of February, 2011

David J. Kappos  
*Director of the United States Patent and Trademark Office*